(12) United States Patent
Kohler et al.

(10) Patent No.: US 11,375,877 B2
(45) Date of Patent: Jul. 5, 2022

(54) METHOD FOR BUILDING A VIDEO BUS, VIDEO BUS LAYOUT, PLUG-IN CARD, ENDOSCOPE AND CORRESPONDING USE

(71) Applicant: Schölly Fiberoptic GmbH, Denzlingen (DE)

(72) Inventors: Alexander Kohler, Freiburg (DE); Daniel Harter, Emmendingen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 159 days.

(21) Appl. No.: 16/713,800

(22) Filed: Dec. 13, 2019

(65) Prior Publication Data

US 2020/0192845 A1    Jun. 18, 2020

(30) Foreign Application Priority Data

Dec. 17, 2018 (DE) .......................... 102018132438.3

(51) Int. Cl.
| | | |
|---|---|---|
| G06F 13/38 | (2006.01) | |
| A61B 1/00 | (2006.01) | |
| G02B 23/24 | (2006.01) | |
| G06F 13/40 | (2006.01) | |
| G09G 3/00 | (2006.01) | |

(52) U.S. Cl.
CPC ...... *A61B 1/00006* (2013.01); *G02B 23/2484* (2013.01); *G06F 13/385* (2013.01); *G06F 13/409* (2013.01); *G09G 3/00* (2013.01)

(58) Field of Classification Search
CPC .. G06F 13/40; G06F 13/4004; G06F 13/4018; G06F 13/4022; G06F 13/4045; G06F 13/409; G06F 13/4068; G06F 13/20; G06F 13/36; G06F 13/4063; G06F 13/385; G02B 23/2484

See application file for complete search history.

(56) References Cited

U.S. PATENT DOCUMENTS

| | | | | |
|---|---|---|---|---|
| 5,343,144 | A * | 8/1994 | Kobayashi | G01R 31/2825 324/750.3 |
| 5,491,830 | A * | 2/1996 | Ferri | G06F 12/0684 710/9 |
| 7,248,470 | B2 * | 7/2007 | Chen | H01R 12/721 361/679.41 |
| 7,480,757 | B2 * | 1/2009 | Atherton | G06F 13/4022 710/307 |
| 7,711,886 | B2 * | 5/2010 | Foster, Sr. | G06F 13/409 710/313 |
| 2004/0221106 | A1 * | 11/2004 | Perego | G11C 5/04 711/115 |
| 2005/0149654 | A1 * | 7/2005 | Holloway | G06F 13/409 710/100 |
| 2011/0060860 | A1 * | 3/2011 | Rimborg | G06F 13/409 710/317 |

(Continued)

FOREIGN PATENT DOCUMENTS

| | | | | |
|---|---|---|---|---|
| WO | WO-0042517 | A1 * | 7/2000 | ........... G06F 13/409 |
| WO | WO-2016122493 | A1 * | 8/2016 | ......... G06F 13/4022 |

*Primary Examiner* — Shawn S An
(74) *Attorney, Agent, or Firm* — Volpe Koenig

(57) ABSTRACT

A video bus (8) that the plug-in cards (7), which are inserted into the individual slots (13), acquire and/or evaluate information, which refers to and/or describes the assigned slot (13) and/or cores (12) already assigned by other plug-in cards (25) or cores (16) which are still free.

22 Claims, 2 Drawing Sheets

(56) References Cited

U.S. PATENT DOCUMENTS

| | | | |
|---|---|---|---|
| 2013/0073775 A1* | 3/2013 | Wade | H04N 7/181 |
| | | | 710/316 |
| 2014/0184770 A1 | 7/2014 | King et al. | |
| 2014/0359558 A1* | 12/2014 | Chamberlain | G06F 8/36 |
| | | | 717/104 |
| 2016/0210254 A1* | 7/2016 | Achlaug | G06F 13/385 |
| 2017/0154008 A1* | 6/2017 | Garibay | G06F 13/4282 |
| 2018/0007788 A1* | 1/2018 | Phares | H05K 5/0069 |

* cited by examiner

METHOD FOR BUILDING A VIDEO BUS, VIDEO BUS LAYOUT, PLUG-IN CARD, ENDOSCOPE AND CORRESPONDING USE

INCORPORATION BY REFERENCE

The following documents are incorporated herein by reference as if fully set forth: German Patent Application No. 10 2018 132 438.3, filed Dec. 17, 2018.

TECHNICAL FIELD

The invention relates to a method for building a video bus, wherein the video bus comprises at least one central processor, which is connected to at least one multicore bus line, wherein the at least one bus line, which comprises a number of cores, is connected to a number of slots, wherein a plug-in card is inserted into one of the slots.

The invention further relates to a video bus layout, with at least one central processor, which is connected to at least one multicore bus line, wherein the at least one bus line comprises a number of cores, with a number of slots, into which plug-in cards can be inserted.

Finally the invention relates to a plug-in card.

BACKGROUND

The use of plug-in cards in video bus layouts is known. One field of application is endoscopy, in which an image is captured digitally using an endoscope and is reworked or conditioned. To this end it has become customary to provide plug-in cards which perform desired reworking or conditioning of an image data stream.

The invention is generally used with the method mentioned in the beginning and the video bus layout mentioned in the beginning, in which one or more central processor(s) is/are present.

SUMMARY

The invention is based on the objective to simplify the configuration of a video bus layout.

To meet this objective, one or more features according to the invention are provided. In particular it is therefore provided according to the invention, for a method for building a video bus of the kind mentioned in the beginning, that the inserted plug-in card ascertains which cores of the bus line are available, and that the plug-in card determines which cores of the at least one bus line are assigned for its own function. In this respect it is of advantage that a self-configuring bus structure is achievable with the aid of simple means.

With one design of the invention it may be provided that the plug-in card, i.e. prior to ascertaining available cores for example, initially ascertains, into which slot it has been inserted. The plug-in card thus simply possesses information concerning which position it has been arranged at in a communication chain. This therefore also makes it possible to automatically take into account peculiarities of the chosen slot.

With one design of the invention it may be provided that the plug-in card informs the central processor which cores are assigned by the plug-in card. Thus utilization of the cores of the video bus can be achieved in a simple manner, and conflicts due to double-use can be avoided or reduced. This may simply pave the way for setting up a central management system relating to the use of the cores.

With one design of the invention it may be provided alternatively or additionally that the plug-in card informs at least one further inserted plug-in card which cores are assigned by the plug-in card. Thus it can be achieved in a decentralized simple manner, that double-assignments of cores are avoided.

With one design of the invention it may be provided that the cores are interrupted at each of the slots. It is thus ensured in a simple manner that no unused slots remain between two plug-in cards or a plug-in card and a central processor. Thus it can be ensured in a simple manner that a user realizes a simple bus topology, in which a chain-type sequence of plug-in cards is formed. Therefore each plug-in card can also influence in a simple manner which data are let through to subordinate plug-in cards. An unequivocal order of plug-in cards in the video bus can thus be defined or set up.

It may for example be provided here that the plug-in card in an inserted position establishes a connection via the plug-in card of the interrupted cores. It can thus be achieved in a simple manner that a signal can be influenced via the video bus by each plug-in card, for example for signal amplification.

With one design of the invention it may be provided that the plug-in card in an inserted position connects the interrupted cores via at least one signal amplifier, respectively. Thus each inserted plug-in card can be used as a repeater. Additionally, this makes it easily possible to take line impedances into account. Avoiding impedance problems is particularly advantageous with high-speed signals as occur for example in video endoscopy.

With one design of the invention it may be provided according to a first option that the plug-in card, via a communications bus, receives information about the respective slot. This makes the avoidance of double assignments easier.

In this respect, with one design of the invention it may be provided alternatively or additionally according to a second option that the plug-in card, via an, e.g. the already mentioned, communications bus, receives information on available cores about the bus line. It can thus be achieved in a simple manner that each plug-in card reserves for itself only cores, which are indeed free. Arbitration methods or testing of individual cores can be waived.

In this respect, with one design of the invention it may be provided alternatively or additionally according to a third option that the plug-in card, via an e.g. the already mentioned, communications bus, issues information about cores of the bus line assigned to itself. This has the advantage that other plug-in cards and/or a central processor can be informed about the assignment of cores.

With each of these options the communications bus may be formed separately from the bus line. Thus it can be avoided that the video bus is influenced by data traffic on the communications bus. The communications process is thus definable individually and independently of the video bus.

The communications process may however also be integrated into the video bus, for example in that a central processor and/or the remaining plug-in cards transmit(s) and/or receive(s) on all cores or at least on all assigned cores of the video bus.

With one design of the invention it may be provided that the communications bus is interrupted at the slots. In this way information can be selectively transferred via the communications bus to a final position in a chain of plug-in cards in a simple manner. Also each plug-in card can thus influence a data transfer to subordinate plug-in cards via the communications bus. In doing so the invention makes use of the fact that due to the interruption at the slots gaps between plug-in cards can be avoided.

In this respect it may be provided that the plug-in card in an inserted position establishes a connection via the plug-in card of the interrupted communications bus. Thus it can be ensured in a simple way that the inserted plug-in cards are connected with each other via a gap-free communications bus.

Each plug-in card thus comprises at least as many signal amplifiers as there are cores in the video bus. If bidirectional data traffic is allowed, each plug-in card has even twice as many signal amplifiers, which at their amplification direction are each aligned in pairs in opposite directions to each other as there are cores in the bus line.

With one design of the invention it may be provided that signal amplifiers on the plug-in card to unassigned cores are switched off when in operation. The advantage here is that energy can be saved when in operation of the signal amplifiers.

With one design of the invention it may be provided that the inserted plug-in card forms a slave on the communications bus on one side facing the central processor. The plug-in card can thus be controlled by the central processor in a simple manner.

To this effect, with one design of the invention it may be provided alternatively or additionally, that the inserted plug-in card forms a master on the communications bus on one side facing away from the processor. The plug-in card can thus be used in a simple manner for controlling further plug in cards. Since according to the invention information is provided as to which plug-in-location has a plug-in card inserted, it is easy to realize an unequivocal assignment to a master function in downward signal direction and a slave function in upward signal direction. It is particularly favorable here if the video bus is interrupted at the slot, as long as no plug-in card has been inserted.

With one design of the invention it may be provided that the plug-in card receives information via at least one further plug-in card, as to whether the further plug-in card is of an input type or an output type. This information can come from the plug-in card or from the central processor. Thus a signal direction of the video bus may be used for example for determining an amplification direction and/or for determining a master and/or slave function. In particular this allows a core assignment at a slot to be recognizable for the plug-in card of the slot in dependence of the type of plug-in card assigning the cores and to be processable, in particular for determining an amplification direction. This also means that a mixed operation can be realized, where individual cores are assigned for an input type and other cores are assigned for an output type.

In this respect it may be provided that the plug-in card, depending on this information, switches an amplification direction of a signal amplifier to a core assigned by the further plug-in card. This has the advantage that a mixed operation with different signal directions can be realized on the videos, wherein amplification can be realized so as to be adapted to the signal direction.

With one design of the invention it may be provided that the at least one bus line comprises an input branch and an output branch, wherein the plug-in card is inserted into a slot of the input branch, if it is of an input type. A clear layout of plug-in cards, which serve to input signals, is thus realizable.

To this effect, with one design of the invention it may be provided alternatively or additionally that the at least one bus line comprises an input branch and an output branch, wherein the plug-in card is inserted into a slot of the output branch, if it is of an output type. A clear layout of plug-in cards, which serve to output signals, is thus realizable.

To solve said objective for a video bus layout according to the invention, the one or more features of the invention directed at a video bus layout are provided. For a video bus layout of the kind mentioned in the beginning it is therefore in particular proposed according to the invention that the cores of the at least one bus line are interrupted at each slot such that a connection of the interrupted cores can be established via the inserted plug-in card. A video bus layout can thus be formed, with which it is easily ensured that slots situated in the signal flow between an assigned slot and a further assigned slot or situated between an assigned slot and a central processor, cannot be left unassigned when in operation. This can simplify the topology of the video bus and can for example be used for simple impedance matching or signal conditioning. This also makes it easier to simply define an order or sequence of the plug-in cards in the video bus.

With one design of the invention it may be provided that the central processor is an FPGA. A low-price and energy-efficient means is thus available for performing for example the method according to the invention and/or the associated bus communication.

However, other processor types may also be used, for example ISP (integrated signal processor), CPU (central processing unit), DSP (digital signal processor) or GPU (graphical processor unit).

With one design of the invention it may be provided that the at least one bus line comprises an input branch and an output branch, wherein a plug-in card is or can be inserted into a slot of the input branch, if it is of an input type. Signal inputs can thus be handled separately. A number of required signal amplifiers on the plug-in card can be reduced in the input branch. Only one signal amplifier per core is required.

To this effect, with one design of the invention it may be provided alternatively or additionally that the at least one bus line comprises an input branch and an output branch, wherein a plug-in card is and/or can be inserted into a slot of the output branch, if it is of an output type. Signal outputs can thus be handled separately. A number of required signal amplifiers on the plug-in card can be reduced in the output branch. Only one signal amplifier per core is required.

With FPGAs it is customary that the high-speed signal lines on the FPGA run in separately from one another at an input and at an output or are connected. A division or separation of input branches and output branches is therefore particularly advantageous in this case.

With these designs it may for example be provided that the input branch is connected to an input of the processor and/or the output branch is connected to an output of the processor. This has the advantage that the input and the output of the processor can be operated separately from one another. Conflicts during data transmission are thus avoidable.

With one design of the invention it may be provided as a first option that a communications bus is formed, via which the plug-in cards receive information about their slot. A simple means is thus provided for offering information to a plug-in card about the current assigned slot. Specific precautions at the slot, for example DIP switches or other encodings such as specific switch encodings may be waived.

To this effect, with one design of the invention it may be provided alternatively or additionally as a second option that a communications bus is formed, via which the plug-in cards receive information about available cores of the bus line. Double assignments are thus avoidable in a simple manner. Specific arbitration methods for detecting and triggering a double assignment may be waived.

To this effect, with one design of the invention it may be provided alternatively or additionally as a third option that a, in particular the already mentioned, communications bus is formed, via which the plug-in cards issue information about cores of the bus line assigned to themselves. Information about which cores are required by the respective plug-in card for its own data traffic can thus be provided in a simple manner to other plug-in cards and/or a central processor.

With one design of the invention it may be provided that a, in particular the already mentioned, communications bus is interrupted at the slots. It can thus be prevented in a simple manner that slots remain inadvertently unused in the communications bus. Inserted plug-in cards can thus be selectively controlled, in particular in that it is possible to count plug-in cards in a signal flow starting with the last plug-in card. Due to the interruption of the communications bus at the slots it can be achieved in a simple manner, in contrast to a T-shaped topology with branching points, that the sequence of the plug-in cards is unequivocally defined by their layout in the slots. Each plug-in card can thus control which information is forwarded to subsequent plug-in cards.

In this respect it may for example be provided that inserted plug-in cards establish a connection of the interrupted communications bus. This permits simple forwarding of information about the communications bus for otherwise interrupted plug-in-locations.

With one design of the invention it may be provided that inserted plug-in cards are set up as repeaters on the at least one bus line. Impedance problems, which could result from excessively long lines on the bus line and/or from too many and too different plug-in cards, can thus be avoided or at least reduced.

To this effect, with one design of the invention it may be provided alternatively or additionally that inserted plug-in cards are set up as repeaters on a, in particular the already mentioned, communications bus. Forwarding of information over the communications bus with sufficient signal strength is thus achievable in a simple manner.

With one design of the invention it may be provided that the video bus layout is equipped with means for executing a method according to the invention, in particular as claimed in one of the claims directed at a method and/or as described above. Thus the advantages of the method according to the invention can be utilized for the video layout according to the invention.

To solve said objective for a plug-in card according to the invention, one or more features of the invention directed at a plug-in card are provided. For a plug-in card of the kind mentioned in the beginning it is therefore in particular proposed according to the invention that the plug-in card comprises contact surfaces for contacting contact elements of a slot, wherein the contact surfaces are connected to at least one pair of contact elements of the slot on the plug-in card. This has the advantage that an interruption in the video bus at the slots can be canceled in a simple manner by inserting a plug-in card. It can thus be directly physically controlled, which slots are assigned and which are not assigned. Therefore, if the slots are filled without gaps as from a position, the slots/the inserted cards can be simply counted as from the end or from the beginning of the bus line. External additional inputs are not required.

With this arrangement the contact surfaces may be assigned to at least one pair of contact elements at a slot position of the slot. A clear and simple looping-through of the signals of the video bus and/or the communications bus can thus be achieved.

The connection of the contact surfaces can for example be made by means of a signal amplifier on the plug-in card. This permits integrated signal amplification and avoids unnecessary signal amplifications outside the plug-in cards. In particular this simply avoids unnecessary signal amplifications outside of assigned branches or sections of the bus line.

It can be preferably provided that the plug-in card is formed as a video plug-in card. It has become evident that the layout as claimed in the invention is particularly favorable precisely for the control and signal amplification of video plug-in cards.

Alternatively or additionally it may be provided that the plug-in card is designed for an inventive video bus layout, in particular as claimed in one of the claims directed at a video bus layout and/or as previously described. Alternatively or additionally it may be provided that the plug-in card is designed for use in a method according to the invention, in particular as claimed in one of the claims directed at a method and/or as previously described. This has the advantage that the advantages of the individual aspects of the invention can be combined with each other.

With one design of the invention it may be provided according to a first option that the plug-in card comprises means for receiving information related to a slot on the plug-in card. This has the advantage that information about the slot, e.g. the slot number or a type of slot, can in particular be provided as signal input or as signal output, for further processing on the plug-in card.

With one design of the invention it may be provided as a second option, alternatively or additionally to the first option, that the plug-in card comprises means for processing information related to a slot on the plug-in card. This has the advantage that the plug-in card itself can ascertain, into which slot it has been inserted.

With one design of the invention it may be provided as a third option, alternatively or additionally to the previous options, that the plug-in card comprises means for receiving information about assigned cores of the bus line on the plug-in card. The plug-in card can thus ascertain in a simple manner which cores are no longer available for communication.

With one design of the invention it may be provided as a fourth option, alternatively or additionally to the previous options, that the plug-in card comprises means for processing information about assigned cores of the bus line on the plug-in card. This has the advantage that the plug-in card can ascertain in a simple manner, without external help, which cores are still free for its own communication.

With one design of the invention it may be provided that an amplification direction of a signal amplifier arranged between two contact surfaces, which are assigned to the slot, can be changed. This has the advantage that the plug-in card can handle looped-through cores in different ways, depending in which direction a signal flow takes place. It is thus possible for example for the signal amplifiers to cores, via which input signals are transmitted, and for the signal amplifiers to cores, via which output signals are transmitted, to be operated in opposite directions.

To this effect, with one design of the invention it may be provided alternatively or additionally that an operating state of a signal amplifier arranged between two contact surfaces, which are assigned to the slot, can be changed. This has the advantage that the plug-in card can be designed so as to be randomly configurable, in order to be adapted to the kind of actually assigned cores and in particular to a transmission direction of the individual cores.

With one design of the invention it may be provided that the plug-in card is designed for ascertaining free cores of the bus line. This means that collisions due to double assignments are automatically avoidable.

To this effect, with one design of the invention, it may be provided alternatively or additionally that the plug-in card is designed for assigning free cores of the bus line. This has the advantage that the plug-in card can automatically, i.e. for example independently of a central processor, assign cores of the bus line for itself.

A preferred application of the inventive method, the inventive video bus layout, and/or the inventive plug-in card may be provided in the context of an endoscope. It has been revealed that particularly with endoscopes or in the field of endoscopy the use of a modular construction, which the invention makes possible, is of particular advantage.

BRIEF DESCRIPTION OF THE DRAWINGS

The invention will now be described in more detail with reference to exemplary embodiments, but is not limited to the exemplary embodiments. Further exemplary embodiments result from a combination of the features of one or more protective claims among each other and/or with one or more features of the exemplary embodiments.

In the highly schematic depiction of the figures.

DETAILED DESCRIPTION

Figure 1:
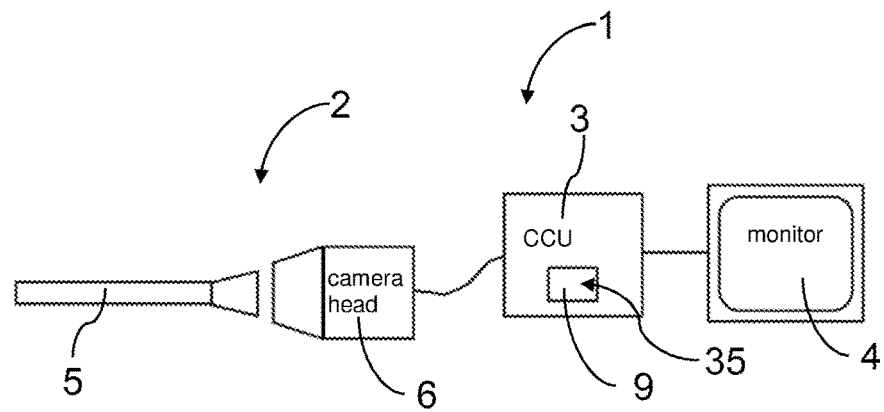
FIG. 1 shows an endoscopy arrangement with an inventive video bus layout for explaining the inventive method.

FIG. 1 shows an endoscopy arrangement denoted as a whole with 1, which in a manner known as such comprises an endoscope 2, a camera control unit 3 and a monitor 4. The endoscope 2 may comprise here an endoscope shaft 5 and a camera head 6. The endoscope shaft 5 and the camera head 6 may be detachably connected to each other or be integrally configured. The endoscope 2 may also comprise an image sensor at the distal end. The endoscope 2 may thus be generally designed as a video endoscope.

The endoscope 2 of the endoscopy arrangement 1 thus produces an image data stream of video data, which is passed to the camera control unit 3 for further processing. Following further processing said video data is displayed on the monitor 4.

In the camera control unit 3, depending on the demands for further processing, such as image resolution, color enhancement, wrong color representation or further processing steps known as such, a mode of operation of the camera control unit 3 can be determined by using modular plug-in cards 7.

Figure 2:
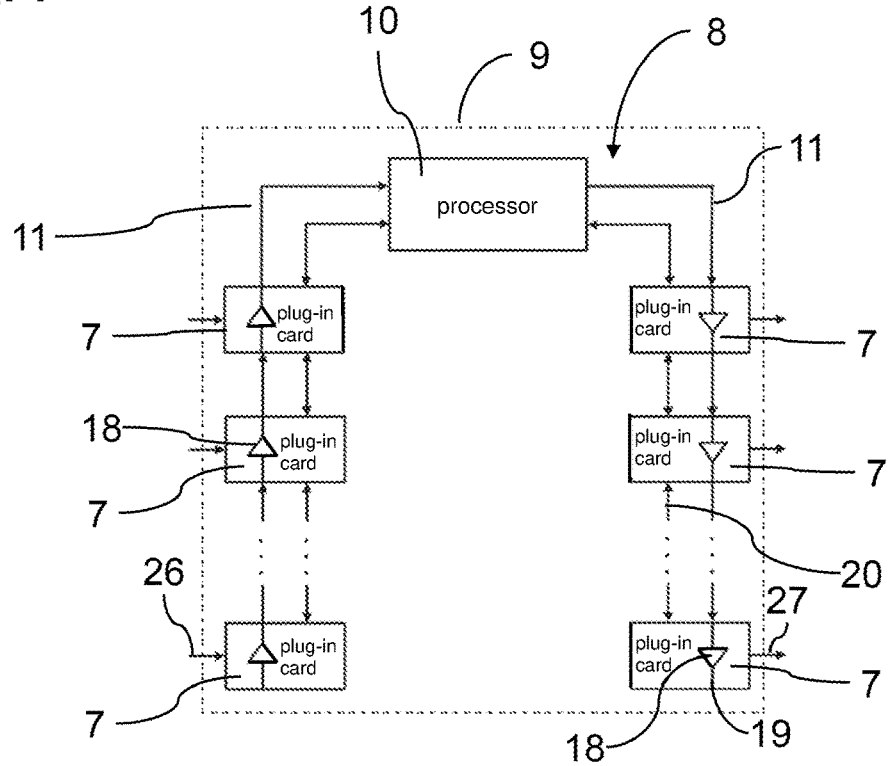
FIG. 2 shows a block diagram of an inventive video bus layout of an endoscopy arrangement according to FIG. 1.

FIG. 2 shows a video bus 8 of a video bus layout 9, such as may be used in for example the camera control unit 3.

The video bus layout 9 has a central processor 10, from which or to which bus lines 11 extend.

Figure 4:
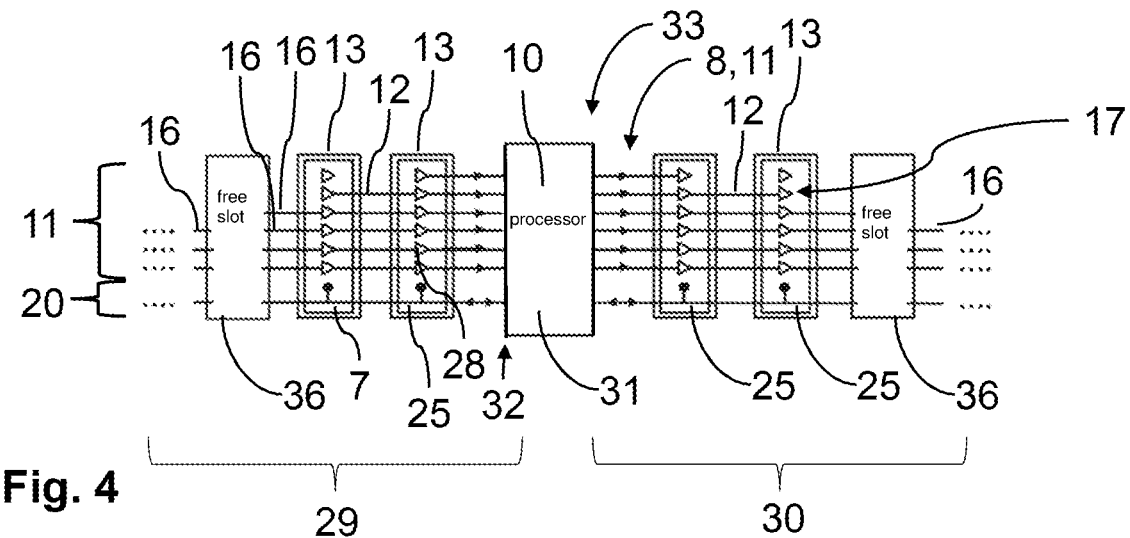
FIG. 4 shows a detail view of an inventive video bus layout.

As can be recognized more accurately in FIG. 4, each bus line 11 comprises a multiplicity of cores 12.

The bus lines 11 connect the central processor 10 to slots 13.

A plug-in card 7 can be inserted into each of these slots 13 in a manner known as such. The respective slot 13 then holds the inserted plug-in card 7 mechanically and contacts the same electrically via contact elements 15, which act upon corresponding contact surfaces 14 of the plug-in card 7.

The inserted plug-in card 7 initially ascertains automatically, in which slot 13 it has been inserted. This may for example be done by reading a corresponding encoding at the slot 13. Alternatively or additionally the invention can make use here of the fact that the respective core 12 is interrupted at the slot 13, as long as no plug-in card 7 has been inserted. The consequence of this is that in a chain starting from the central processor 10 the last assigned slot 13 can be ascertained, since this is characterized in that the plug-in card 7 can communicate in one direction, but not in the other direction. Alternatively or additionally each plug-in card 7 can interrupt an information flow between the slots 13 at its own slot 13 in order to, in this way, prevent subsequent plug-in cards also from being able to detect information. In this way a successive allocation of slot numbers is achievable.

Alternatively the required information can be exchanged also via a communications bus 20 described further below.

Subsequently the plug-in card 7 ascertains which of the cores 12 have been assigned by other plug-in cards. This may be done for example by trial communication via the individual cores 12. This may also be done e.g. in that the plug-in card 7 communicates with the central processor 10, which may keep a list of the assigned cores 12. If the assigned cores 12 or the free cores 16 have been ascertained, the plug-in card 7 occupies a corresponding number of the cores depending on the demand of the free cores 16.

Given the case that the central processor 10 keeps a list of assigned cores, the plug-in card 7 can now signal the assigned cores to the central processor 10. It may also be provided that the central processor 10 sends recurringly corresponding requests over the video bus 8 and evaluates replies or reactions.

Figure 3:
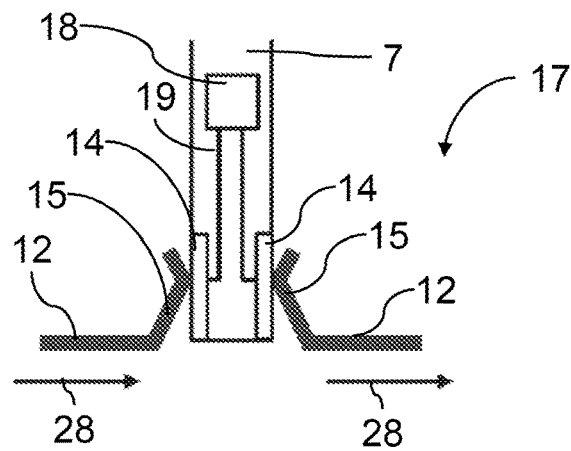
FIG. 3 shows a highly simplified sectional view through an inventive plug-in card to a video bus layout according to FIG. 2.

As already mentioned, the cores 12 are interrupted at each slot 13, as shown in FIG. 3.

To the contact elements 15, which belong in pairs to a slot position 17 at the plug-in position 13, there correspond matching contact surfaces 14, which are formed on both sides of the plug-in card 7.

These contact surfaces 14 are electrically connected in pairs to a signal amplifier 18 on the plug-in card 7, so that the inserted plug-in card 7 establishes an electrical connection 19 of the interrupted core 12.

Signal amplifiers 18 on a plug-in card 7, which are connected to unassigned or free cores 16, are deactivated.

The video bus layout 9 also comprises a communications bus 20. The communications bus 20 is guided parallel to the video bus 8 and is also interrupted at each slot 13. The communications bus 20 is thus arranged separately from the video bus 8.

Analogously to the video bus 8 an inserted plug-in card 7 establishes a connection to the interrupted communications bus 20. With this arrangement the two ends of the interrupted communication bus 20 may be connected to different communications units or different inputs of communications units on the plug-in card 7, which can communicate with each other.

The communications bus 20 serves to exchange information about slots 13, assigned and free cores 16, and of further information described in more detail further below.

In a further example the communications bus 20 may also be of uninterrupted design, wherein a branch-off is formed at each slot 13.

It can be stated that each plug-in card 7 processes as a slave 22 on a side 21 facing the processor 10, in particular on the communications bus 20, whilst said card works as a master 24 on a side 23 facing away from the processor 10.

This master 24 can then control a subsequent further plug-in card 25, which in relation to this master 24 is again operated as a slave.

Figure 5:
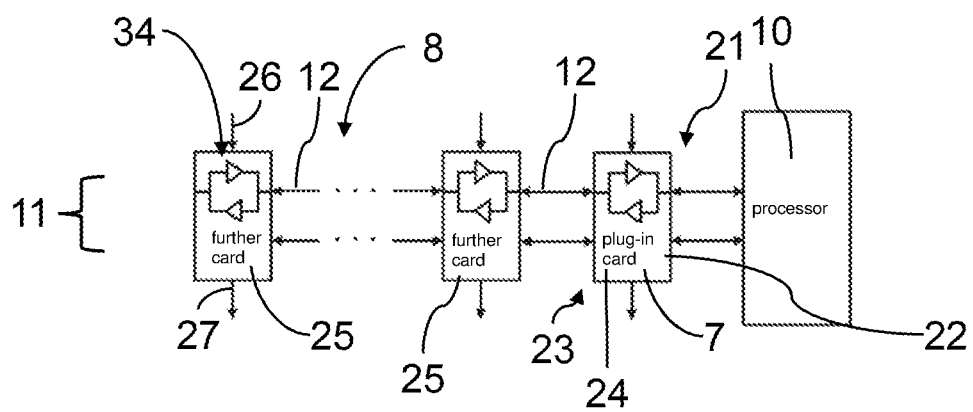
FIG. 5 shows a detail view of a further inventive video bus layout.

It is shown in FIG. 5 that the plug-in cards 7 each comprise signal inputs 26 and signal outputs 27.

The cores 12 are operated accordingly in a bidirectional manner. The connection 19 is thus established by a pair of signal amplifiers 18 connected in opposite directions, which amplify the signals on the video bus 8/the communications bus 20 in an amplification direction 28, respectively.

Figure 6:
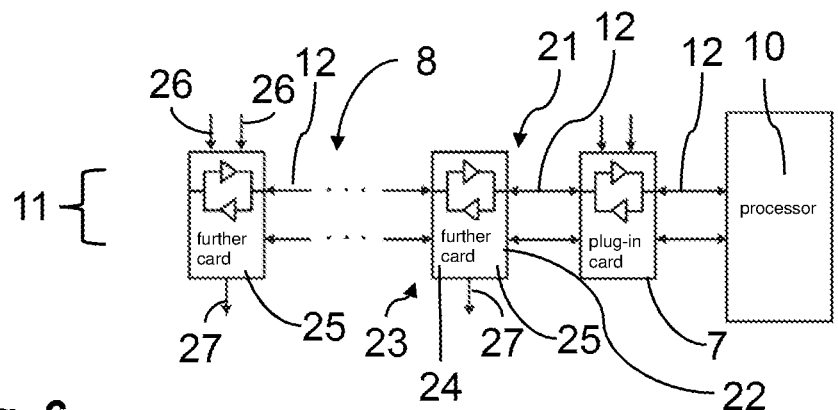
FIG. 6 shows a detail view of a third inventive video bus layout.

FIG. 6 shows the case, where the plug-in cards 7 each comprise a different number of signal inputs 26 and signal outputs 27.

It may thus be the case that individual cores 12 forward signals only in one direction, depending on whether a signal input 26 or a signal output 27 is realized on the associated plug-in card 7, to which this core 12 is assigned. The previous plug-in cards 7 then configure their signal amplifiers 18 in such a way that an amplification direction 28 matches the respective data flow direction of the core 12.

Plug-in cards 7, which comprise only signal inputs 26, may be called input-type plug-in card. Plug-in cards 7, which comprise only signal outputs 27, may be called output-type plug-in card. The terms "input type" and "output type" may also be used in an analog manner for individual cores 12.

FIG. 4 reveals that the video bus 8 comprises an input branch 29 and an output branch 30. Only input-type plug-in cards 7 are arranged in the input branch 29, whereas only output-type plug-in cards 7 are arranged in the output branch 30.

The communications bus 20 in the exemplary embodiment is however bidirectional.

The information as to whether a plug-in card 7 or a core 12, due to its assignment, is of the input type or the output type, can be forwarded via the communications bus 20 to the further plug-in cards 25, which switch their signal amplifiers 18 to a correspondingly correct amplification direction 28. Expressed in simplified terms this means that a signal amplifier 18 for each core, the amplification direction 28 of said signal amplifier does not match the signal flow direction, is switched off.

The central processor 10 is designed as a FPGA 31. Here the division into input branch 29 and output branch 30 is particularly favorable, because the FPGA 31 can therefore be provided with pure signal inputs 32/pure signal outputs 33.

With the signal amplifiers 18 already discussed in detail each plug-in card 7 thus functions as a repeater 34 for further plug-in cards 25. Each plug-in card 7 is equipped with a processor and/or memory 35 for receiving and/or for processing information about assigned cores 12, about free cores 16, about an amplification direction 28 on the respective core 12, about the number or identifier of the respective slot 13, in which the plug-in card 7 inserts, and/or about further information such as for example protocol details or video format details.

FIG. 4 shows a free slot 36 in that the cores 12 are still interrupted.

With a video bus 8 it is thus provided according to the invention that the plug-in cards 7, which are inserted into the individual slots 13, acquire and/or evaluate information, which refers to and/or describes the assigned slot 13 and/or cores 12 already assigned by other plug-in cards 25 or still free cores 16.

REFERENCE LIST 1 endoscopy arrangement
2 endoscope
3 camera control unit
4 monitor
5 endoscope shaft
6 camera head
7 plug-in card
8 video bus
9 video bus layout
10 processor
11 bus line
12 core
13 slot
14 contact surface
15 contact element
16 free core
17 slot position
18 signal amplifier
19 connection
20 communications bus
21 facing side
22 slave
23 facing-away side
24 master
25 further plug-in card
26 signal input
27 signal output
28 amplification direction
29 input branch
30 output branch
31 FPGA
32 signal input of 31
33 signal output of 31
34 repeater
35 processor and/or memory for receiving and/or for processing information
36 free slot

The invention claimed is:

1. A method for building a video bus (8), comprising:
providing at least one central processor (10), and connecting the at least one central processor to at least one multicore bus line (11),
the at least one bus line (11) comprises a number of cores (12) and is connected to a number of slots (13),
inserting a plug-in card (7) into one of the slots (13),
the inserted plug-in card (7) ascertaining by at least one of trial communication via individual ones of the cores (12) or by communicating with the central processor (10), which of the cores (12) of the at least one bus line (11) have been assigned by other plug-in cards and which of the cores (12) are available, the plug-in card (7) setting those cores (12) of the at least one bus line (11) to be assigned for its own function, by occupying a corresponding number of the available cores (12),
such that a self-configuring video bus (8) is obtained, and
the inserted plug-in card (7), prior to ascertaining the available cores (12), ascertaining which of the slots (13) it has been inserted into, and the plug-in card (7) informing at least one of the central processor (10) or at least one further inserted plug-in card (25) which cores (12) are assigned by the plug-in card (7).

2. The method as claimed in claim 1, further comprising interrupting the cores (12) at each of the slots (13), and the plug-in card (7) in an inserted position establishing a connection via the plug-in card (7) of the interrupted cores (12).

3. The method as claimed in claim 2, wherein the plug-in card (7) in the inserted position connects the interrupted cores (12) via at least one signal amplifier (18), respectively.

4. The method as claimed in claim 1, wherein the plug-in card (7), via a communications bus (20), at least one of (a) receives information about at least one of the respective slot (13) or about the available cores (12) of the bus line (11) or (b) issues information about the cores (12) of the bus line (11) assigned to itself.

5. The method as claimed in claim 4, further comprising the communications bus (20) being interrupted at the slots (13), and the plug-in card (7) in an inserted position establishing a connection via the plug-in card (7) of the interrupted communications bus (20).

6. The method as claimed in claim 4, further comprising switching off signal amplifiers (18) on the plug-in card (7) to unassigned cores (16) when in operation.

7. The method as claimed in claim 4, further comprising the inserted plug-in card (7) at least one of (a) forming a slave (22) on the communications bus (20) on one side facing the central processor (10) or (b) forming a master (24) on the communications bus (20) on one side facing away from the processor (10).

8. The method as claimed in claim 1, further comprising the plug-in card (7) receiving information via at least one further plug-in card (25), as to whether the further plug-in card (25) is of an input type or an output type, and depending on said information, the plug-in card (7) switches an amplification direction (28) of a signal amplifier (18) to the core (12) assigned by the further plug-in card (25).

9. The method as claimed in claim 1, wherein the at least one bus line (11) comprises an input branch (29) and an output branch (30), the plug-in card (7) is inserted into one of the slots (13) of the input branch (29), if it is of an input type, or is inserted into one of the slots (13) of the output branch (30), if it is of an output type.

10. A video bus layout (9), comprising:
at least one central processor (10), which is connected to at least one multicore bus line (11),
the at least one bus line (11) comprises a number of cores (12), with a number of slots (13), into which plug-in cards (7) are adapted to be inserted, and
the cores (12) of the at least one bus line (11) are interrupted at each of the slots (13) such that a connection (19) of the interrupted cores (12) is adapted to be established via the inserted plug-in card (7), and wherein
the video bus layout (9) is built according to the method of claim 1.

11. The video bus layout (9) as claimed in claim 10, wherein the central processor (10) is an FPGA (31).

12. The video bus layout (9) as claimed in claim 10, wherein the at least one bus line (11) comprises an input branch (29) and an output branch (30), the plugin card (7) is adapted to be inserted into one of the slots (13) of the input branch (29), if it is of an input type, or is adapted to be inserted into one of the slots (13) of the output branch (30), if it is of an output type, and the input branch (29) is connected to an input of the processor (10) and the output branch (30) is connected to an output of the processor (10).

13. The video bus layout (9) as claimed in claim 10, wherein a communications bus (20) is formed, via which the plug-in cards (7) are adapted to at least one of (a) receive information about at least one of an associated one of the slots (13) or about available cores (16) of the bus line (11), or (b) issue information about cores (12) of the bus line (11) assigned to the plug-in card (7).

14. The video bus layout (9) as claimed in claim 13, wherein the communications bus (20) is interrupted at the slots (13), and the inserted plug-in cards (7) are adapted to establish a connection (19) of the interrupted communications bus (20).

15. The video bus layout (9) as claimed in claim 10, wherein inserted plug-in cards (7) are set up as repeaters (34) on at least one of the at least one bus line (11) or a communications bus (20).

16. A method of using the video bus layout (9) as claimed in claim 10, comprising
inserting the plug-in card (7) into one of the slots (13), and
the inserted plug-in card (7) ascertaining by at least one of trial communication via the individual cores (12) or by communicating with the central processor (10), which of the cores (12) of the at least one bus line (11) have been assigned by other plug-in cards and which of the cores (12) are available, and
the plug-in card (7) setting those cores (12) of the at least one bus line (11) to be assigned for its own function, by occupying a corresponding number of the available cores (12).

17. A plug-in card (7) for use with a video bus layout (9) as claimed in claim 10, the plug-in card (7) comprises:
contact surfaces (14) configured for contacting contact elements (15) of a respective one of the slots (13),
the contact surfaces (14) are connected to at least one pair of contact elements (15) of the respective one of the slots (13) by a signal amplifier (18) on the plug-in card (7) and the plug-in card (7) is configured to
ascertain by at least one of trial communication via the individual cores (12) or by communicating with the central processor (10), which of the cores (12) of at least one bus line (11) have been assigned to the other plug-in cards and which of the cores (12) are available and to
set the cores (12) of the at least one bus line (11) to be assigned to its own function, by occupying a corresponding number of the available cores (12).

18. The plug-in card (7) as claimed in claim 17, wherein the plug-in card (7) comprises at least one of a processor or memory for at least one of receiving or processing information (35) related to at least one of the slots (13) or assigned cores (12) of the bus line (11) on the plug-in card (7).

19. The plug-in card (7) as claimed in claim 17, wherein at least one of an amplification direction (28) or an operating state of a signal amplifier (18) arranged between two of the contact surfaces (14), which are assigned to the slot (13), are changeable.

20. The plug-in card (7) as claimed in claim 17, wherein the plug-in card (7) is adapted for at least one of ascertaining or assigning free cores (16) of the bus line (11).

21. The method as claimed in claim 1, wherein the video bus (8) is for use with an endoscope (2).

22. An endoscope (2) comprising
a video bus layout (9), the video bus layout (9) comprising
    at least one central processor (10), which is connected to at least one multicore bus line (11),
    the at least one bus line (11) comprises a number of cores (12), with a number of slots (13), into which plug-in cards (7) are adapted to be inserted,
    wherein a plug-in card (7) is inserted into one of the slots (13), and
    the cores (12) of the at least one bus line (11) are interrupted at each of the slots (13) such that a connection (19) of the interrupted cores (12) is adapted to be established via the inserted plug-in card (7), and
the plug-in card (7) comprises
    contact surfaces (14) for contacting contact elements (15) of a respective one of the slots (13), the contact surfaces (14) are connected to at least one pair of contact elements (15) of the respective one of the slots (13) by a signal amplifier (18) on the plug-in card (7),
    wherein the inserted plug-in card (7) is configured to ascertain by at least one of
        trial communication via individual ones of the cores (12) or
        by communicating with the central processor (10),
    which of the cores (12) of the at least one bus line (11) have been assigned by other plug-in cards and which of the cores (12) are available, and
the plug-in card (7) setting those cores (12) of the at least one bus line (11) to be assigned for its own function, by occupying a corresponding number of the available cores (12),
such that a self-configuring video bus (8) is obtained; and
wherein the inserted plug-in card (7) is further configured such that, prior to ascertaining the available cores (12), the inserted plug-in card ascertains which of the slots (13) it has been inserted into, and the plug-in card (7) informs at least one of the central processor (10) or at least one further inserted plug-in card (25) which cores (12) are assigned by the plug-in card (7).

* * * * *